United States Patent
Sambasivam et al.

(10) Patent No.: US 10,294,317 B2
(45) Date of Patent: May 21, 2019

(54) PRESSURE SENSITIVE ADHESIVES WITH AMPHIPHILIC COPOLYMERS

(75) Inventors: Mahesh Sambasivam, Skillman, NJ (US); Joseph C. Salamone, San Antonio, TX (US); Ann Beal Salamone, San Antonio, TX (US); Xiang Yu, San Antonio, TX (US)

(73) Assignee: Convatec Technologies Inc., Las Vegas, NV (US)

(*) Notice: Subject to any disclaimer, the term of this patent is extended or adjusted under 35 U.S.C. 154(b) by 627 days.

(21) Appl. No.: 13/382,227

(22) PCT Filed: Jul. 7, 2010

(86) PCT No.: PCT/US2010/041180
§ 371 (c)(1),
(2), (4) Date: Jan. 4, 2012

(87) PCT Pub. No.: WO2011/005839
PCT Pub. Date: Jan. 13, 2011

(65) Prior Publication Data
US 2012/0109036 A1 May 3, 2012

Related U.S. Application Data

(60) Provisional application No. 61/223,534, filed on Jul. 7, 2009, provisional application No. 61/228,023, filed on Jul. 23, 2009.

(51) Int. Cl.
| | | |
|---|---|---|
| A61F 13/00 | (2006.01) | |
| A61L 24/04 | (2006.01) | |
| C08L 33/14 | (2006.01) | |
| C08L 83/04 | (2006.01) | |
| C08F 230/08 | (2006.01) | |

(52) U.S. Cl.
CPC .......... C08F 230/08 (2013.01); A61L 24/046 (2013.01); *A61F 2013/00702* (2013.01)

(58) Field of Classification Search
USPC ........ 602/41–43, 52, 54; 424/443, 445, 448; 523/111; 604/389
See application file for complete search history.

(56) References Cited

U.S. PATENT DOCUMENTS

| 4,693,935 A | 9/1987 | Mazurek |
| 5,045,060 A * | 9/1991 | Melsky et al. ........... 604/288.02 |
| 5,103,812 A * | 4/1992 | Salamone et al. .............. 602/52 |
| 7,014,627 B2 * | 3/2006 | Bierman ........................ 604/174 |
| 2004/0102744 A1 * | 5/2004 | Fattman ........................ 604/344 |
| 2008/0268242 A1 * | 10/2008 | Zhou et al. ............... 428/355 N |
| 2009/0114342 A1 | 5/2009 | Aoki et al. |

FOREIGN PATENT DOCUMENTS

| EP | 0412770 A1 | 2/1991 |
| WO | WO-2011/005839 | 1/2011 |

OTHER PUBLICATIONS

Oda et al; "Block versus Random Amphiphilic Copolymers as Antibacterial Agents"; Biomacromolecules 2011, 12, 3581-3591.*
Oda et al; "Block versus Random Amphiphilic Copolymers as Antibacterial Agents".*
Canadian Patent Application No. 2766116 Official Action dated Aug. 25, 2016.

* cited by examiner

*Primary Examiner* — Ophelia A Hawthorne
*Assistant Examiner* — Caitlin A Carreiro
(74) *Attorney, Agent, or Firm* — Wilson Sonsini Goodrich & Rosati

(57) ABSTRACT

A silicone pressure sensitive adhesive with amphiphilic copolymers for maintaining adhesion in a moist environment. The amphiphilic copolymers for silicone adhesives include at least one silicone moiety and at least one hydrophilic segment. Such adhesives are applicable to securing medical devices to human skin.

5 Claims, No Drawings

PRESSURE SENSITIVE ADHESIVES WITH AMPHIPHILIC COPOLYMERS

BACKGROUND OF THE INVENTION

Silicone pressure sensitive adhesives are widely used in transdermal drug delivery, wound dressings, scar dressings, and other healthcare applications. These adhesives are typically a condensation product of silicate resin and polydimethylsiloxane (PDMS) fluid, or a reactive blend of vinyl- and hydride-containing PDMS and a silicate resin cured via hydrosilylation reaction (Dow Corning Literature, *Silicone Pressure Sensitive Adhesives* (2002)). These adhesives are biocompatible, gentle on the skin, and securely attach medical devices to the body when the environment is dry. However, under moist conditions such as during skin perspiration, the hydrophobic silicone adhesives lose their adhesion to skin, which can lead to the dressing detaching from the body prematurely.

There is a need to improve the adhesion of these adhesives to skin in the presence of moisture. Traditionally, adhesion of skin adhesives under moist environments has been accomplished by adding water absorbing fillers such as hydrocolloids to pressure sensitive adhesives. The hydrocolloid fillers absorb moisture and soften, providing wet tack, thereby improving the adhesion to skin longer. However, the disadvantages of this approach are the reduction in the dry peel strength and tack properties of the adhesive due to the presence of hard fillers. In addition, because of the affinity of the fillers for water, they dissolve and leach out of the adhesive, which can leave a slimy residue on the skin after the dressing removal.

In order to improve the adhesion of silicone adhesives under a moist environment and to overcome the drawbacks of previous approaches, the present approach is to add a suitable amphiphilic silicone copolymer to a silicone pressure sensitive adhesive. An ideal amphiphilic silicone copolymer suitable for such applications should possess high cohesive strength, high moisture vapor transmission rate (MVTR), high pressure sensitive adhesion to surfaces, maintain adhesion even under moist conditions, and should not leach out components or leave a residue. Commercially available amphiphilic silicone copolymers are typically based on grafted poly(ethylene glycol). These copolymers are low molecular weight liquids, which are typically used as surfactants or defoamers. Addition of such low molecular weight copolymers can affect the adhesive performance because of surface migration under moist conditions and lead to a reduction in adhesion.

Several amphiphilic silicone copolymers have been reported in the literature. Recently, G. Edrodi and J. P. Kennedy published the synthesis of amphiphilic conetworks of poly(ethylene glycol) (PEG) and polydimethylsiloxane (PDMS) (G. Edrodi and J. P. Kennedy, *J. Polym. Sci. Part A: Polym. Chem.*, 43, 4954-4963 (2005)). The amphiphilic conetworks exhibited swelling in water and hexane indicating bi-continuous phases.

Yildiz, et al. synthesized block copolymer of poly(vinyl pyrrolidone)-poly(dimethyl siloxane)-poly(vinyl pyrrolidone) (J. C. Kim, M. Song, S. Park, E. Lee, M. Rang, and H. Ahn, *J. Appl. Polym. Sci.*, 85, 2244-2253 (2002)). They prepared a di-isocyanate terminated PDMS which was then end-capped with t-butyl peroxide. This was used as a macroinitiator for N-vinyl pyrrolidone polymerization. The resulting copolymers showed lower glass transition temperature (Tg) than the homopolymer poly(vinyl pyrrolidone).

Graiver, et al. used aldehyde-functional silicones as reactive sites for vinyl copolymerization in the presence of a copper redox system (D. Graiver, G. T. Decker, Y. Kim, F. J. Hamilton, and H. J. Harwood, *Silicon Chemistry*, 1, 107-120 (2002)). Several graft and block copolymers including polymethacrylic acid and polyacrylic acid were incorporated into the silicone polymer. These polar segments were formed by the thermal decomposition of the t-butyl ester substituted polyacrylate segments.

Yilgor, et al. synthesized triblock copolymers of polycaprolactone-PDMS, and poly(2-ethyl-2-oxazoline)-PDMS (I. Yilgor, W. P. Steckle, E. Yilgor, R. G. Freelin, and J. S. Riffle, *J. Polym. Sci. Part A: Polym. Chem.*, 27, 3673-3690 (1989)). For the caprolactone, hydroxyl-terminated PDMS was used as a macroinitiator, and for the oxazoline copolymers, benzyl chloride-terminated PDMS was used. The resulting copolymers with a silicone content of about 30-50% were shown to reduce the surface tension of plastics, such as PET, PMMA, and polyurethane.

Yildiz, et al. synthesized poly(N-isopropylacrylamide) hydrogels using diacrylate-terminated PDMS as the crosslinker (Y. Yildiz, N. Uyanik, and C. Erbil, J. Macromol. *Sci., Part A: Pure and Applied Chemistry*, 43, 1091-1106 (2006)). The resulting hydrogels were found to have higher compression moduli compared to the conventional crosslinker, N,N'-methylene bis-acrylamide. This was attributed to the hydrophobic interactions between PDMS segments in the network.

DETAILED DESCRIPTION OF THE INVENTION

The present invention includes silicone pressure sensitive adhesive compositions having novel amphiphilic silicone copolymers. The silicone pressure sensitive adhesive compositions according to the present invention are suitable for adhering to biological surfaces. The pressure sensitive adhesive includes an amphiphilic copolymer that is a reaction product of at least one silicone monomer or oligomer and at least one hydrophilic or amphiphilic monomer or oligomer. such that the amphiphilic copolymer:

does not dissolve in aqueous medium, and has a molecular weight greater than 10,000 g/mol The silicone monomer is a methacryloylalkylsiloxysilane, vinylalkylsiloxysilane, vinylalkoxysilane, and combinations thereof.

The silicone oligomer is polydimethylsiloxane with reactive groups selected from hydride, vinyl, methacrylate, acrylate, epoxy, carbinol, mercapto, acetoxy, amino, isocyanato, halide, hydroxyl, and combinations thereof.

The hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, reactive polyethers, polyisocyanates, polyesters, polyamides, polypeptides, polysaccharides, polyurethanes, and combinations thereof.

A silicone pressure sensitive adhesive composition as described above is suitable for adhering medical devices to biological surfaces when it comprises 0.1-100% of an amphiphilic copolymer of at least one silicone monomer or oligomer and at least one hydrophilic or amphiphilic monomer or oligomer that does not leach out in the presence of moisture. Such an adhesive is applicable for adhering medical devices, such as ostomy appliances, wound dressings, securement devices for surgical devices, intravenous delivery devices, catheters and infusion devices to human skin.

The amphiphilic copolymer structure is a block, alternating, random, branched, grafted, or a combination.

According to the present invention, a silicone pressure sensitive adhesive is blended with a sufficient amount of amphiphilic silicone copolymer so as to yield an adhesive that stays adhered under moist conditions and will not leach the copolymer in moisture. The invention also includes the synthesis of an amphiphilic silicone copolymer that is a pressure sensitive adhesive by itself.

Amphiphilic Copolymers:

The amphiphilic copolymers are based on a polymerizable silicone monomer copolymerized with hydrophilic and/or amphiphilic monomers.

Synthesis of Amphiphilic Tris(trimethylsiloxysilyl propyl) Methacrylate (TRIS) Copolymers The typical procedure for the synthesis of the poly(TRIS)-based random copolymers, via free radical polymerization, is as follows, using poly(TRIS-co-N,N'-dimethylaminoethyl methacrylate) (DMAEMA) (3:1 wt) as an example: 4.5 g TRIS and 1.5 g of DMAEMA were added into a 25 mL pressure resistant reaction flask. Then 0.045 g VAZO™ 67 was transferred into the flask. To the flask was then added 14 g ethyl acetate to afford a 30 wt % solution. The mixture was gently shaken until a clear solution was obtained. It was then flushed with nitrogen for 2 minutes, sealed, and let sit in a 65° C. oil bath for 6 hours. Following this, the solvent was evaporated at room temperature for 36 hours to produce a more viscous solution, which was then cast onto polyethylene film and further dried for 2 days, and finally vacuum dried. The copolymer, a soft, tacky solid, was washed in deionized water and H$_2$O/methanol 50/50 v/v mixture.

Similarly, other TRIS copolymers were made with methacrylic acid (MAA), N-vinylcaprolactam (NVCL), N-isopropylacrylamide (NIPAM), N-hydroxyethylacrylamide (NHEA), and methacrylate-terminated PDMS.

Pressure Sensitive Adhesive Compositions with Amphiphilic Silicone Copolymers

EXAMPLE 1

The typical procedure for the preparation of silicone gel adhesive containing amphiphilic copolymer is as follows. A 1:1 ratio of NUSIL® MED-6345 Part A and Part B were taken. Then poly(TRIS-co-NIPAM) (3:1 monomer wt ratio) solution in HMDS was added so that the adhesive gel would eventually contain 5 wt % of solid copolymer. The mixture was thoroughly stirred and then coated on a polyurethane film and allowed to dry for 1 hour for evaporation of solvent. Later the adhesive was cured at 60° C. in the oven for 3 hours. In the case of 100% amphiphilic copolymer, the copolymer was dissolved in HMDS, coated onto to a polyurethane film and then dried in the oven. A 1-inch by 1.5-inch strip of the adhesive was tested on human subject for adhesion under dry and wet environment. For dry adhesion, the tape was secured to the abdominal area for 8 hours prior to removal. For wet adhesion, the tape was attached to abdominal skin of the human subject and then tape removed after an aerobic activity for 40-60 minutes. The results of the adhesion studies under dry and wet conditions are shown in Table 1.

TABLE 1

| No. | Sample Description | *Dry Adhesion | **Wet Adhesion |
|---|---|---|---|
| 1 | Control: MED ™ 6345 50/50 Parts A/B cured at 60° C. for 3 hr (17-65) | Adhered well | Completely delaminated |
| 2 | MED ™ 6345 50/50 Parts A/B + 5 wt % Poly(TRIS-co-NIPAM) 5 mol % NIPAM Cured at 60° C.–3 hr (17-83) | Adhered well | Good adhesion; no residue |
| 3 | Control: MED ™ 6345 30/70 Parts A/B cured at 60° C. for 3 hr (17-65) | Poor adhesion-delaminated completely | Completely delaminated |
| 4 | MED ™-6345 50/50 Parts A/B + 10 wt % Poly(TRIS-co-DMAEMA) 5 mol % DMAEMA Cured at 60° C.–3 hr (17-83) | Adhered well | Weak adhesion; no residue |
| 5 | Poly(TRIS-co-Methacrylic acid) w/5 mol % methacrylic acid | Adhered very well- cold flow at edges | Very good adhesion- left a lot of residue |

*Adhesion to abdominal skin for 8 hrs prior to removal (1.5" adhesive strip)
**Adhesion to abdominal skin followed by 40-60 minutes of activity prior to removal while perspiring
MED ™-6345 is a two-part tacky silicone gel from NUSIL ® Technology.
VAZO ™ 67 is a free radical initiator from DUPONT ®.

Adhesives, 2, 4 and 5 are sufficient to secure an ostomy appliance, wound dressing, infusion device or other securement device to human skin.

Other Inventive Examples

The dry adhesion was measured at room temperature with a finger. The range of 0-5 was used (5=excellent adhesion, 0=no adhesion) for qualifying adhesion. The wet adhesive strength was measured using a tongue depressor which had been soaked in water for 5 min (and dipped in water and taken out before each measurement). The polymer films were cast from 20 wt % solutions in ethyl acetate, dried for 5 h, and equilibrated at 35° C. in the incubator overnight in a moist environment, then taken out and immediately measured. (The wet adhesion for all other materials was measured this way unless otherwise mentioned.) The cohesive strength indicates the ability of the adhesive film to be removed from the substrate without leaving residue or breaking apart. Cohesive strength was measured on a scale of 1 to 5 (5=no residue with intact film, 1=low cohesive strength with extensive residue remaining on the host substrate)

TABLE 2

Properties of blends of MED-6345(50/50) with poly(TRIS/NVCL)

| Formulation | Weight Ratio | Wet Adhesion | Cohesive Strength |
|---|---|---|---|
| MED ™-6345 (50/50) | 100:0 | 3 | 1 |
| MED ™-6345 (50/50) + poly(TRIS/NVCL) (3.6/1) | 100:5 | 3.5 | 1 |

TABLE 3

Properties of TRIS/MAA polymers (unpurified)

| Polymer (unpurified) | Dry adhesions[a] | Wet adhesion | Cohesive strength |
|---|---|---|---|
| TRIS/MAA (97/3) | 1/2.5 | 0 | 3.5 |
| TRIS/MAA (97.5/2.5) | 2.5/3.5 | 0.5 | 3.5 |
| TRIS/MAA (98/2) | 3/4 | 0.5 | 3 |
| TRIS/MAA (98.5/1.5) | 3/4 | 1 | 2.5 |
| TRIS/MAA (99/1) | 4/>5 | 1.5 | 1.5 |

[a] adhesion after pressing for ~0.5 seconds/adhesion after pressing for ~10 seconds

TABLE 4

Properties of TRIS/MAA polymers (unpurified, heated at 60° C. overnight)

| Polymer (unpurified) | Dry adhesions[a] | Wet adhesion | Cohesive strength |
|---|---|---|---|
| TRIS/MAA (97/3) | 0/0.5 | 0 | 5 |
| TRIS/MAA (97.5/2.5) | 0.5/1 | 0 | 4.5 |
| TRIS/MAA (98/2) | 1/2 | 0 | 4 |
| TRIS/MAA (98.5/1.5) | 1.5/2.5 | 0.5 | 4 |
| TRIS/MAA (99/1) | 3/3.5 | 1 | 3.5 |

[a] adhesion after pressing for ~0.5 seconds/adhesion after pressing for ~10 seconds

TABLE 5

Properties of TRIS/MAA polymers (purified, not heated)

| Polymer (purified) | Dry adhesions[a] | Wet adhesion | Cohesive strength |
|---|---|---|---|
| TRIS/MAA (97/3) | 0/0 | 0 | 5 (brittle) |
| TRIS/MAA (97.5/2.5) | 0/0 | 0 | 5 (brittle) |
| TRIS/MAA (98/2)-10 mol % MAA | 0/0 | 0 | 5 (almost brittle) |
| TRIS/MAA (98.5/1.5) | 0/0.5 | 0 | 5 |
| TRIS/MAA (99/1)-5 mol % MAA | 1/1.5 | 0 | 4.5 |
| TRIS/MAA (99.5/0.5) | 1.5/2 | 0 | 4 |
| TRIS/MAA (99.75/0.25) | 1.5/2.5 | 0.5 | 4 |
| TRIS/MAA (99.875/0.125) | 2/3 | 0.5 | 3.5 |
| TRIS/MAA (99.9375/0.0625) | 3/3.5 | 1 | 2.5 |
| TRIS (100%) | 3.5/5 | 1 | 1.5 |

[a] adhesion after pressing for ~0.5 seconds/adhesion after pressing for ~10 seconds

TABLE 6

Properties of purified TRIS/NIPAM copolymers

| Polymer (purified) | Dry adhesions[a] | Wet adhesion | Cohesive strength |
|---|---|---|---|
| TRIS/NIPAM (5/1) | 0/0 | 0 | 5 (brittle) |
| TRIS/NIPAM (6/1) | 0/0.5 | 0 | 5 (almost brittle) |
| TRIS/NIPAM (7/1) | 0.5/1.5 | 0 | 5 |
| TRIS/NIPAM (8/1) | 1/2 | 0 | 5 |
| TRIS/NIPAM (12/1) | 1/2.5 | 0 | 5 |
| TRIS/NIPAM (15/1) | 1.5/3 | 0 | 4.5 |

TABLE 7

Properties of NIPAM/PDMS-macromonomer copolymers

| Polymer | Dry adhesions[a] | Wet adhesion | Cohesive strength |
|---|---|---|---|
| NIPAM/PDMS-macromonomer (1/2.5) | 0/0.5 | 0 | 5 (slightly rubbery) |
| NIPAM/PDMS-macromonomer (1/3) | 0/0.5 | 0 | 4.5 (somewhat rubbery) |
| NIPAM/PDMS-macromonomer (1/5) | 3/4.5 | 1 | 1 (rubbery but weak) |
| NIPAM/PDMS-macromonomer (1/7) | N/A | N/A | 0 |
| NIPAM/PDMS-macromonomer (1/10) | N/A | N/A | 0 |

PDMS-macromonomer purchased from GELEST ®, Inc.

We believe that this is the first time that a unique amphiphilic silicone copolymer has been synthesized that is used in a pressure sensitive adhesive composition and is capable of securely adhering medical devices to the body.

Tables 1-7 indicate that the pressure sensitive adhesives with amphiphilic copolymers of the present invention adhere well under dry and wet conditions. Furthermore, adhesion of these compositions to skin shows an improvement over silicone adhesives without the copolymers.

We claim:

1. A silicone pressure sensitive adhesive composition suitable for adhering a medical device to skin comprising 0.1-100% of an amphiphilic random copolymer that is a free radical polymerization reaction product of at least one silicone monomer or oligomer and at least one hydrophilic or amphiphilic monomer or oligomer, such that the amphiphilic copolymer:
   a) does not dissolve in aqueous medium,
   b) has a molecular weight greater than 10,000 g/mol; and
   c) does not leach out in the presence of moisture; and wherein
   the silicone monomer is methacryloylalkylsiloxysilane, vinylalkylsiloxysilane, vinylalkoxysilane, or combinations thereof;
   the silicone oligomer is polydimethylsiloxane with reactive groups selected from hydride, vinyl, methacrylate, acrylate, epoxy, carbinol, mercapto, acetoxy, amino, isocyanato, halide, hydroxyl, and combinations thereof; and
   the hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, reactive polyethers, polyisocyanates, polyesters, polyamides, polypeptides, polysaccharides, polyurethanes, and combinations thereof.

2. An ostomy device comprising a silicone pressure sensitive adhesive composition on a body contacting surface of the device and suitable for adhering the device to the body, wherein the pressure sensitive adhesive comprises an amphiphilic random copolymer that is a free radical polymerization reaction product of at least one silicone monomer or oligomer and at least one hydrophilic or amphiphilic monomer or oligomer such that the amphiphilic copolymer:

a) does not dissolve in aqueous medium; and
b) has a molecular weight greater than 10,000 g/mol; and wherein the silicone monomer is methacryloylalkylsiloxysilane, vinylalkylsiloxysilane, vinylalkoxysilane, or combinations thereof;

the silicone oligomer is polydimethylsiloxane with reactive groups selected from hydride, vinyl, methacrylate, acrylate, epoxy, carbinol, mercapto, acetoxy, amino, isocyanato, halide, hydroxyl, and combinations thereof;

the hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, reactive polyethers, polyisocyanates, polyesters, polyamides, polypeptides, polysaccharides, polyurethanes, and combinations thereof.

3. A wound dressing comprising a silicone pressure sensitive adhesive composition on a body contacting surface of the dressing and suitable for adhering the dressing to the body, wherein the pressure sensitive adhesive comprises an amphiphilic random copolymer which is a free radical polymerization reaction product of at least one silicone monomer or oligomer and at least one hydrophilic or amphiphilic monomer or oligomer such that the amphiphilic copolymer:

a) does not dissolve in aqueous medium; and
b) has a molecular weight greater than 10,000 g/mol; and wherein the silicone monomer is methacryloylalkylsiloxysilane, vinylalkylsiloxysilane, vinylalkoxysilane, or combinations thereof;

the silicone oligomer is polydimethylsiloxane with reactive groups selected from hydride, vinyl, methacrylate, acrylate, epoxy, carbinol, mercapto, acetoxy, amino, isocyanato, halide, hydroxyl, and combinations thereof;

the hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, reactive polyethers, polyisocyanates, polyesters, polyamides, polypeptides, polysaccharides, polyurethanes, and combinations thereof.

4. A securement device for attaching surgical devices, catheters, and intravenous delivery devices to the body comprising a silicone pressure sensitive adhesive composition on a body contacting surface of the device, and suitable for adhering the securement device wherein the pressure sensitive adhesive comprises an amphiphilic random copolymer which is a free radical polymerization reaction product of at least one silicone monomer or oligomer and at least one hydrophilic or amphiphilic monomer or oligomer such that the amphiphilic copolymer:

a) does not dissolve in aqueous medium; and
b) has a molecular weight greater than 10,000 g/mol; and wherein the silicone monomer is methacryloylalkylsiloxysilane, vinylalkylsiloxysilane, vinylalkoxysilane, or combinations thereof;

the silicone oligomer is polydimethylsiloxane with reactive groups selected from hydride, vinyl, methacrylate, acrylate, epoxy, carbinol, mercapto, acetoxy, amino, isocyanato, halide, hydroxyl, and combinations thereof;

the hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, reactive polyethers, polyisocyanates, polyesters, polyamides, polypeptides, polysaccharides, polyurethanes, and combinations thereof.

5. An infusion device comprising a silicone pressure sensitive adhesive composition on a body contacting surface of the device, and suitable for adhering the infusion device to the body, wherein the pressure sensitive adhesive comprises an amphiphilic random copolymer that is a free radical polymerization reaction product of at least one silicone monomer or oligomer and at least one hydrophilic or amphiphilic monomer or oligomer such that the amphiphilic copolymer:

a) does not dissolve in aqueous medium; and
b) has a molecular weight greater than 10,000 g/mol; and wherein the silicone monomer is methacryloylalkylsiloxysilane, vinylalkylsiloxysilane, vinylalkoxysilane, or combinations thereof;

the silicone oligomer is polydimethylsiloxane with reactive groups selected from hydride, vinyl, methacrylate, acrylate, epoxy, carbinol, mercapto, acetoxy, amino, isocyanato, halide, hydroxyl, and combinations thereof;

the hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, reactive polyethers, polyisocyanates, polyesters, polyamides, polypeptides, polysaccharides, polyurethanes, and combinations thereof.

* * * * *